United States Patent [19]

Dinkel

[11] 4,337,342
[45] Jun. 29, 1982

[54] PROCESS FOR THE PREPARATION OF 3-PICOLINE

[75] Inventor: Rolf Dinkel, Visp, Switzerland

[73] Assignee: Lonza Ltd., Gampel/Valais, Switzerland

[21] Appl. No.: 263,042

[22] Filed: May 12, 1981

[30] Foreign Application Priority Data

May 23, 1980 [CH] Switzerland .......................... 4052/80

[51] Int. Cl.³ .................. C07D 213/09; C07D 213/10; C07D 213/12
[52] U.S. Cl. .................................................... 546/251
[58] Field of Search .......................................... 546/251

[56] References Cited

U.S. PATENT DOCUMENTS 2,769,007 10/1956 Bamford .............................. 546/251

FOREIGN PATENT DOCUMENTS

| 1903878 | 9/1969 | Fed. Rep. of Germany ...... 546/251 |
| 2337087 | 2/1974 | Fed. Rep. of Germany ...... 546/251 |
| 534494 | 3/1941 | United Kingdom ................ 546/251 |
| 971174 | 9/1964 | United Kingdom ................ 546/251 |
| 1182705 | 3/1970 | United Kingdom ................ 546/251 |
| 1208569 | 10/1970 | United Kingdom ................ 546/251 |

*Primary Examiner*—Robert T. Bond
*Attorney, Agent, or Firm*—Fisher, Christen & Sabol

[57] ABSTRACT

A process for the preparation of 3-picoline wherein a mixture acetaldehyde and/or crotonaldehyde with formaldehyde is reacted in the presence of an ammonium salt at a temperature of 180° to 280° C. in a closed vessel. The mixture is in the liquid phase.

24 Claims, No Drawings

PROCESS FOR THE PREPARATION OF 3-PICOLINE

BACKGROUND OF THIS INVENTION

1. Field of this Invention

This invention relates to a process for the preparation of 3-picoline.

2. Prior Art

Pyridine bases are important intermediates in the chemical industry, for example, for the preparation of nicotinic acid or nicotinamide. Various processes for the preparation of pyridine bases are known.

2-Methyl-5-ethylpyridine is nowadays industrially manufactured by means of a liquid phase process from acetaldehyde or paraldehyde and ammonia in the presence of a large variety of catalysts, for example, ammonium salts. Small amounts of 2-picoline and 4-picoline are formed as by-products.

2-Picoline and 4-picoline are nowadays prepared by gas phase reactions from acetaldehyde and ammonia at a temperature of about 400° C. using fixed-bed or fluidized-bed catalysts based upon aluminum silicate.

For the production of pyridine and of 3-picoline, which is constantly gaining in importance, gas phase reactions are nowadays employed. In such reactions the formation of 2-picoline and 4-picoline is suppressed, in favor of 3-picoline, by adding formaldehyde to the acetaldehyde. These reactions, again, are carried out in a fixed bed or fluidized bed using aluminum silicate as the catalyst at a temperature of about 400° C. Using such processes, yields of 3-picoline in the order of magnitude of at most 40 to 44 percent are achieved. At the same time large amounts of pyridine are formed.

Instead of saturated aldehydes, it is also known that unsaturated aldehydes, for example acrolein or crotonaldehyde, can be used as the starting materials. Such reactions take place in the gas phase at high temperatures; the yields are substantially of the same order as when using saturated aldehydes as the starting material.

BROAD DESCRIPTION OF THIS INVENTION

It is an object of this invention to prepare 3-picoline in high yields, while suppressing the formation of pyridine as much as possible. Other objects and advantages of this invention are set out herein or are obvious herefrom to one ordinarily skilled in the art.

The objects and advantages of this invention are achieved by the process of this invention.

This invention involves a process for the production of 3-picoline. In the process, acetaldehyde and/or crotonaldehyde, mixed with formaldehyde, is reacted in the presence of an ammonium salt, in the liquid phase, at a temperature of 180° to 280° C. in a closed vessel. The process of this invention achieves preparation of 3-picoline in high yields, with as much as possible suppression of the formation of pyridine.

For the purposes of this invention, acetaldehyde includes its polymers, for example paraldehyde, and formaldehyde includes its polymers, for example trioxane.

If liquid starting materials which are not miscible with one another, for example paraldehyde together with aqueous formaldehyde, are used, it is advantageous to employ small amounts of homogenizing agents, such as alcohols, cyclic ethers or, preferably, previously formed 3-picoline, in order to homogenize the mixture.

The process according to this invention surprisingly gives yields of about 60 to 70 percent of 3-picoline, while the formation of pyridine is virtually completely suppressed (to less than 1 percent). The by-products formed are 3-ethylpyridine and small amounts of 2,5-dimethylpyridine, 3,5-dimethylpyridine and 2-methyl-5-ethylpyridine.

The process of this invention is advantageously carried out with a molar ratio of acetaldehyde to formaldehyde of 1:0.5 to 1:1.2, preferably of 1:0.8 to 1:1.0. If crotonaldehyde is used instead of acetaldehyde, the molar ratio of crotonaldehyde to formaldehyde correspondingly becomes 1:1.0 to 1:2.4.

The reaction temperatures are advantageously 180° to 280° C., appropriately 205° to 240° C., and preferably 225° to 235° C.

The reaction is carried out in the liquid phase (aqueous phase) under the autogenous pressure resulting from the reaction in a closed vessel at the predetermined temperature. It is advantageous to stir the batch during the reaction.

Suitable ammonium salts are, for example, ammonium acetate, ammonium fluoride, ammonium chloride, ammonium bifluoride, ammonium borate, ammonium benzoate, ammonium molybdate and ammonium sulfide. Preferably the ammonium salts are ammonium phosphates. These ammonium salts can also be formed in situ from the corresponding components. The amount of the ammonium salt employed, as an aqueous solution with a concentration ranging from 1 to 80 percent by weight of the ammonium salt, is 0.5 to 3 moles per mole of aldehyde, advantageously 0.6 to 1.0 mole per mole of aldehyde.

In a variant of the process of this invention, ammonia, as an aqueous solution or a gas, is employed in addition to the ammonium salt.

The starting pH value of the aqueous reaction solution is advantageously between 7 and 9.

The aldehyde is advantageously added at the rate at which it is consumed. Thus, for example, it is advantageous, when carrying out the reaction in a 2-liter vessel and employing 350 ml of aldehyde, to add the latter continuously in the course of 29 to 92 minutes. Under different conditions, the periods of addition appropriate to these are to be chosen.

At the end of the desired reaction period, the temperature is reduced to approximately room temperature and the 3-picoline is isolated from the reaction mixture in a conventional or suitable manner. One method comprises extracting the organic material from the aqueous reaction mixture by means of an organic solvent, for example, benzene, toluene, xylene, methylene chloride, chloroform, ether and the like. The organic solvent is then evaporated off and 3-picoline is obtained by fractional distillation. Within the scope of this invention, any other suitable method can also be used to separate off and isolate the product.

A further advantage of the novel process according to this invention is that the aqueous ammonium salt phase, obtained after extracting the reaction mixture with an organic solvent, and after re-enrichment of it with ammonia, can be recycled to the reactor. The aqueous salt phase consists of the amount of water originally present in the salt solution, the unconverted ammonium salt, the acid of the ammonium salt participating to the reaction, and one mole of water for each mole of aldehyde consumed in the reaction. The aqueous salt phase is therefore concentrated by means of any known process, for example by evaporation, so as to remove the water formed as a consequence of the condensation reaction. The salt phase is then re-enriched by reacting the aqueous solution with liquid ammonia at ambient temperature to form the ammonium salt.

Though this invention has been described in the form of a batchwise process it is also possible within the scope of this invention to continuously carry out the process. In one embodiment of a continuous process, the reactants are continuously introduced into a suitable pressure reactor, from which a portion of the reaction mixture is continuously withdrawn. The reaction products are isolated from this portion, and unconverted reactants are then replenished and recycled to the reaction vessel. The continuous process can be carried out in any reaction which permits intimate mixing of the reactants, with vigorous stirring, for example, in a continuously-stirred tank reactor.

By way of summary, this invention involves a process for the preparation of 3-picoline from an aldehyde mixture of acetaldehyde and formaldehyde, in the liquid phase.

DETAILED DESCRIPTION OF THIS INVENTION

As used herein, all percentages, proportions, parts and ratios are on a weight basis unless otherwise stated herein or otherwise obvious herefrom to one ordinarily skilled in the art.

EXAMPLE 1

1,130 ml of a 3.37 molar aqueous solution of diammonium hydrogen phosphate (pH 8.3) is heated to 235° C. in a 2-liter autoclave and stirred at 1,500 rpm. A mixture of 114.1 g of acetaldehyde and 219.2 g of a 32.0%-strength aqueous formaldehyde solution (molar ratio=1.:0.90) is pumped continuously into the above solution in the course of 63 minutes, during which the reaction pressure varies between 38 and 40 bar. After completion of the addition of the aldehyde mixture, the reaction batch is stirred for a further 10 minutes at 235° C. and is then cooled to room temperature. Finally, it is extracted with 3×100 ml of toluene and the combined toluene extracts are subjected to analysis by gas chromatography, which reveals the following products, in yields based on acetaldehyde (A) or formaldehyde (F) as employed: pyridine 0.9 percent (A); 3-picoline 68.0 percent (F); 3-ethylpyridine 15.0 percent (A); 2,5-lutidine 2.5 percent (A); 3,5-lutidine 1.4 percent (F); and 2-methyl-5-ethylpyridine 0.6 percent (A).

All of the gas-chromatographic analyses are carried out using an internal standard, and taking into account area correction factors.

EXAMPLE 2

1,130 ml of a 3.38 molar aqueous solution of diammonium hydrogen phosphate (pH 8.3) is heated to 230° C. in a 2-liter autoclave and stirred at 1,500 rpm. A mixture of 121.8 g of acetaldehyde and 208.2 g of a 32.0%-strength aqueous formaldehyde solution (molar ratio=1:0.80) is pumped continuously into the above solution in the course of 60 minutes, during which the reaction pressure varies between 33 and 35 bar. After completion of the addition of the aldehyde mixture, the reaction batch is stirred for a further 10 minutes at 230° C. and is then cooled to room temperature. Finally, it is extracted with 3×100 ml of toluene and the combined toluene extracts are subjected to analysis by gas chromatography, which reveals the following products, in yields based on acetaldehyde (A) or formaldehyde (F) as employed: pyridine 0.8 percent (A); 3-picoline 62.5 percent (F); 3-ethylpyridine 22.6 percent (A): 2,5-lutidine 3.6 percent (A); 3,5-lutidine 0.9 percent (F); and 2-methyl-5-ethylpyridine 1.9 percent (A).

EXAMPLE 3

1,060 ml of a 3.37 molar aqueous solution of diammonium hydrogen phosphate (pH 8.3) is heated to 222° C. in a 2-liter autoclave and stirred at 1,200 rpm. A mixture of 108.4 g of paraldehyde, 222.4 g of a 33.2%-strength aqueous formaldehyde solution (molar ratio=1:3.00) and 73.1 g of 3-picoline (homogenizing agent) is pumped continuously into the above solution in the course of 68 minutes. After completion of the addition of the aldehyde mixture, the reaction batch is stirred for a further 10 minutes at 222° C. and is then cooled to room temperature. Finally, it is extracted with 3×100 ml of toluene and the combined toluene extracts are subjected to analysis by gas chromatography, which reveals the following products, in yields based on paraldehyde as employed: pyridine 0.8 percent; 3-picoline 55.2 percent (excluding the material used for homogenization); 3-ethylpyridine 10.0 percent; 2,5-lutidine 1.9 percent; 3,5-lutidine 1.4 percent; and 2-methyl-5-ethylpyridine 1.9 percent.

EXAMPLE 4

25.0 g of gaseous ammonia is passed into 1,140 ml of a 10.0 molar aqueous ammonium acetate solution (pH 8.1); and the mixture is then heated to 230° C. in a 2-liter autoclave and stirred at 1,500 rpm. A mixture of 122.2 g of acetaldehyde and 208.2 g of a 32.0%-strength aqueous formaldehyde solution (molar ratio=1:0.80) is pumped continuously into the autoclave in the course of 58 minutes, during which the reaction pressure varies between 27 and 29 bar. After completion of the addition of the aldehyde mixture, the reaction batch is stirred for a further 10 minutes at 230° C. and is then cooled to room temperature. Finally, the homogeneous reaction mixture is subjected to analysis by gas chromatography, which reveals the following products, in yields based on acetaldehyde (A) or formaldehyde (F) as employed: pyridine 0.9 percent (A); 3-picoline 44.8 percent (F); 3-ethylpyridine 19.1 percent (A); 2,5-lutidine 4.0 percent (A); 3,5-lutidine 0.4 percent (F); and 2-methyl-5-ethylpyridine 1.7 percent (A).

EXAMPLE 5

1,140 ml of a 3.40 molar aqueous ammonium acetate solution (pH 7.4) is heated to 230° C. in a 2-liter autoclave and stirred at 1,500 rpm. A mixture of 122.2 g of acetaldehyde and 208.2 g of a 32.0%-strength aqueous formaldehyde solution (molar ratio=1:0.80) is pumped continuously into the above solution in the course of 59 minutes, during which the reaction pressure varies between 26 and 28 bar. After completion of the addition of the aldehyde mixture, the reaction batch is stirred for a further 10 minutes at 230° C. and is then cooled to room temperature, and brought to pH 8.1 with gaseous ammonia. Finally, the reaction mixture, which is now homogeneous, is subjected to analysis by gas chromatography, which reveals the following products, in yields based on acetaldehyde (A) or formaldehyde (F) as employed: pyridine 1.3 percent (A); 3-picoline 53.4 percent (F); 3-ethylpyridine 14.8 percent (A); 2,5-lutidine 4.1 percent (A); 3,5-lutidine 0.7 percent (F); and 2-methyl-5-ethylpyridine 1.9 percent (A).

EXAMPLE 6

1,140 ml of a 3.40 molar aqueous solution of diammonium hydrogen phosphate (pH 8.35) is heated to 230° C. in a 2-liter autoclave and stirred at 1,500 rpm. A mixture of 117.7 g of acetaldehyde, 64.0 g of trioxane and 30.0 g of 3-picoline (homogenizing agent) (calculated molar ratio of acetaldehyde:formaldehyde = 1:0.78) is pumped continuously into the above solution in the course of 74 minutes, during which the reaction pressure varies between 32 and 34 bar. After completion of the addition of the educt mixture, the reaction batch is stirred for a further 10 minutes at 230° C. and is then cooled to room temperature. Finally, it is extracted with 3×100 ml of methylene chloride and the combined methylene chloride extracts are subjected to analysis by gas chromatography, which reveals the following products, in yields based on acetaldehyde (A) or trioxane (F) as employed, depending on the theoretical aldehyde requirement: pyridine 0.7 percent (A); 3-picoline 23.8 percent (F) (excluding the material used for homogenization); 3-ethylpyridine 35.1 percent (A); 2,5-lutidine 6.4 percent (A); 3,5-lutidine 0.2 percent (F); and 2-methyl-5-ethylpyridine 23.3 percent (A).

EXAMPLE 7

1,140 ml of a 3.40 molar aqueous solution of diammonium hydrogen phosphate (pH 8.35) is heated to 230° C. in a 2-liter autoclave and stirred at 1,500 rpm. A mixture of 117.7 g of paraldehyde, 64.0 g of trioxane, 130 g of water and 100 g of ethanol (calculated molar ratio of acetaldehyde:formaldehyde = 1:0.79) is pumped continuously into the above solution in the course of 58 minutes, during which the reaction pressure varies between 32 and 38 bar. After completion of the addition of the educt mixture, the reaction batch is stirred for a further 10 minutes at 230° C. and is then cooled to room temperature. Finally, it is extracted with 3×100 ml of methylene chloride and the combined methylene chloride extracts are subjected to analysis by gas chromatography, which reveals the following products, in yields based on paraldehyde (A) or trioxane (F) as employed, depending on the theoretical aldehyde requirement: pyridine 0.6 percent (A); 3-picoline 19.1 percent (F); 3-ethylpyridine 36.0 percent (A); 2,5-lutidine 7.1 percent (A); 3,5-lutidine 0.2 percent (F): and 2-methyl-5-ethylpyridine 23.9 percent (A).

EXAMPLE 8

1,140 ml of a 3.40 molar aqueous solution of diammonium hydrogen phosphate (pH 8.35) is heated to 230° C. in a 2-liter autoclave and stirred at 1,500 rpm. A mixture of 64.4 g of crotonaldehyde, 39.2 g of acetaldehyde and 213.3 g of a 30.3%-strength aqueous formaldehyde solution (molar ratio of crotonaldehyde:acetaldehyde = 1:1; calculated molar ratio of acetaldehyde:formaldehyde = 1:0.79 is pumped continuously into the above solution in the course of 60 minutes, during which the reaction pressure varies between 32 and 33 bar. After completion of the addition of the aldehyde mixture, the reaction batch is stirred for a further 10 minutes at 230° C. and is then cooled to room temperature. Finally, it is extracted with 3×100 ml of methylene chloride and the combined methylene chloride extracts are subjected to analysis by gas chromatography, which reveals the following products, in yields based on acetaldehyde and crotonaldehyde (A) or formaldehyde (F) as employed, depending on the theoretical aldehyde requirement: pyridine 1.0 percent (A); 3-picoline 53.5 percent (F); 3-ethylpyridine 21.6 percent (A); 2,5-lutidine 5.9 percent (A); 3,5-lutidine 0.7 percent (F); and 2-methyl-5-ethylpyridine 2.8 percent (A).

EXAMPLE 9

1,700 ml of a 3.41 molar aqueous solution of diammonium hydrogen phosphate (pH 8.3) is heated to 230° C. in a 2-liter autoclave and stirred at 1,500 rpm. Into this solution is metered, by means of a first pump (delivering 360.7 g/hour), a mixture of 2,214 g of acetaldehyde and 3,985 g of a 30.5%-strength aqueous formaldehyde solution (molar ratio = 1:0.81). At the end of one hour, a second pump (delivering 1,325.7 g/hour) is additionally switched on, to meter a 3.41 molar aqueous solution of diammonium hydrogen phosphate (pH 8.3) into the mixture. The reaction mixture then begins to overflow, through a pipe attached to the autoclave cover, into a collecting vessel heated to the same temperature. After about 15 minutes, both pumps are stopped, the weights of the educt vessels are recorded, the reaction mixture which has overflowed is drained off into a cooling vessel, and the pumps are then restarted. This procedure is repeated every 60 minutes, so that one fraction is obtained each hour. The reaction pressure, measured in the interim, varies between 33 and 35 bar. After completion of the experiment, fractions 5 to 12 are worked up. In each case, the organic phase is first separated off and the aqueous phase is extracted three times with 100 ml of methylene chloride. The extracts are combined with the above-mentioned organic phase and the aqueous phase which thereupon again separates out is extracted by shaking with a further 60 ml of methylene chloride. All the methylene chloride extracts of fractions 5 to 12 are then combined and analyzed by gas chromatography, using an internal standard and area correction factors. This reveals the following products, with the yields being based, depending on the theoretical aldehyde requirement, either on acetaldehyde (A) or on formaldehyde (F): pyridine 1.2 percent (A); 3-picoline 64.1 percent (F); 3-ethyl-pyridine 21.0 percent (A); 2,5-lutidine 3.5 percent (A); 3,5-lutidine 1.1 percent (F); and 2-methyl-5-ethylpyridine 1.6 percent (A).

What is claimed is:

1. A process for the preparation of 3-picoline which comprises reacting a liquid-phase mixture of acetaldehyde and/or crotonaldehyde with formaldehyde, in the presence of an ammonium salt, at a temperature of 180° to 280° C. in a closed vessel.

2. The process as claimed in claim 1 wherein a molar ratio of acetaldehyde to formaldehyde of 1:0.5 to 1:1.2 is employed.

3. The process as claimed in claim 1 or claim 2 wherein the ammonium salt is an ammonium phosphate.

4. The process as claimed in claim 3 wherein the reaction temperature is from 205° to 240° C.

5. The process as claimed in claim 4 wherein the ammonium salt is employed in aqueous solution at a concentration of 2.9 to 3.7 moles/l.

6. The process as claimed in claim 1 wherein the reaction temperature is from 205° to 240° C.

7. Process as claimed in claim 1 wherein the ammonium salt is employed in aqueous solution at a concentration of 2.9 to 3.7 moles/l.

8. Process as claimed in claim 1 wherein the acetaldehyde is paraldehyde.

9. Process as claimed in claim 1 wherein the formaldehyde is trioxane.

10. Process as claimed in claim 1 wherein a homogenizing agent is present, the homogenizing agent being an alcohol or a cyclic ether.

11. Process as claimed in claim 1 wherein the liquid-phase mixture contains 3-picoline as a homogenizing agent.

12. Process as claimed in claim 1 wherein the ammonium salt is ammonium acetate, ammonium fluoride, ammonium chloride, ammonium bifluoride, ammonium borate, ammonium benzoate, ammonium molybdate, ammonium sulfide or diammonium hydrogen phosphate.

13. Process as claimed in claim 1 wherein the starting pH value of the reaction solution is between 7 and 9.

14. Process as claimed in claim 1 wherein water is present in the reaction solution.

15. Process as claimed in claim 1 wherein the acetaldehyde and/or crotonaldehyde is added to the reaction solution at the rate at which it is consumed.

16. Process as claimed in claim 1 wherein ammonia, as an aqueous solution or a gas, is employed in addition to the ammonium salt.

17. Process as claimed in claim 1 wherein 0.5 to 3 moles of the ammonium salt is used per mole of acetaldehyde and/or crotonaldehyde.

18. Process as claimed in claim 1 wherein the reaction is conducted on a continuous basis.

19. Process for the preparation of 3-picoline which consists of reacting a liquid-phase mixture of acetaldehyde and/or crotonaldehyde with formaldehyde, in the presence of an ammonium salt, at a temperature of 180° to 280° C. in a closed vessel, the molar ratio of acetaldehyde to formaldehyde being from 1:0.5 to 1:1.2.

20. The process as claimed in claim 19 wherein the ammonium salt is an ammonium phosphate.

21. The process as claimed in claim 20 wherein the reaction temperature is from 205° to 240° C.

22. The process as claimed in claim 21 wherein the ammonium salt is employed in aqueous solution at a concentration of 2.9 to 3.7 moles/l.

23. The process as claimed in claim 19 wherein the reaction temperature is from 205° to 240° C.

24. Process as claimed in claim 19 wherein the ammonium salt is employed in aqueous solution at a concentration of 2.9 to 3.7 moles/l.

* * * * *